United States Patent
Krauss

(10) Patent No.: US 10,591,433 B2
(45) Date of Patent: Mar. 17, 2020

(54) PRODUCTION METHOD FOR A GAS SENSOR AND CORRESPONDING GAS SENSOR

(71) Applicant: Robert Bosch GmbH, Stuttgart (DE)

(72) Inventor: Andreas Krauss, Tuebingen (DE)

(73) Assignee: Robert Bosch GmbH, Stuttgart (DE)

(*) Notice: Subject to any disclaimer, the term of this patent is extended or adjusted under 35 U.S.C. 154(b) by 147 days.

(21) Appl. No.: 15/551,939

(22) PCT Filed: Jan. 13, 2016

(86) PCT No.: PCT/EP2016/050508
§ 371 (c)(1),
(2) Date: Aug. 18, 2017

(87) PCT Pub. No.: WO2016/142080
PCT Pub. Date: Sep. 15, 2016

(65) Prior Publication Data
US 2018/0031507 A1     Feb. 1, 2018

(30) Foreign Application Priority Data
Mar. 11, 2015   (DE) .................. 10 2015 204 311

(51) Int. Cl.
*G01N 27/12*   (2006.01)
*B05D 7/00*    (2006.01)

(52) U.S. Cl.
CPC ............ *G01N 27/128* (2013.01); *B05D 7/52* (2013.01); *G01N 27/12* (2013.01)

(58) Field of Classification Search
CPC ......... G01N 27/12; G01N 27/128; B05D 7/52
See application file for complete search history.

(56) References Cited

U.S. PATENT DOCUMENTS

2007/0155037 A1   7/2007   Chou et al.
2008/0134753 A1*  6/2008   Jun ..................... G01N 27/128
                                                         73/23.2

FOREIGN PATENT DOCUMENTS

CN    101119924 A    2/2008
CN    102072850 A    5/2011
CN    104049006 A    9/2014
(Continued)

OTHER PUBLICATIONS

Guha, Prasanta K., et al. "Novel design and characterisation of SOI CMOS micro-hotplates for high temperature gas sensors." Sensors and Actuators B: Chemical 127.1 (2007): 260-266.*
(Continued)

*Primary Examiner* — Robert J Eom
(74) *Attorney, Agent, or Firm* — Norton Rose Fulbright US LLP; Gerard Messina

(57) ABSTRACT

A gas sensor, having: a substrate; a heatable membrane configured on a substrate front side of the substrate; at least three electrodes disposed on a membrane surface of the membrane; a first coating configured on an area of the membrane surface, at least two of the at least three electrodes contacting the first coating; a second coating configured on the first coating and on an area of the membrane surface, at least two of the at least three electrodes contacting the second coating, and at least one of the at least two electrodes that contact the second coating being different from the at least two electrodes that contact the first coating.

7 Claims, 4 Drawing Sheets

(56) References Cited

FOREIGN PATENT DOCUMENTS

| DE | 60004843 T2 | 6/2004 |
|---|---|---|
| DE | 102007059653 A1 | 6/2004 |
| DE | 202007007387 U1 | 8/2007 |
| EP | 1192452 A | 4/2002 |
| EP | 2207029 A1 | 7/2010 |
| EP | 2533037 A1 | 12/2012 |
| EP | 2713157 A1 | 4/2014 |

OTHER PUBLICATIONS

Viricelle, Jean-Paul, et al. "Selectivity improvement of semi-conducting gas sensors by selective filter for atmospheric pollutants detection." Materials Science and Engineering: C 26.2-3 (2006): 186-195.*

International Search Report dated Mar. 14, 2016, of the corresponding International Application PCT/EP2016/050508 filed Jan. 13, 2016.

* cited by examiner

PRODUCTION METHOD FOR A GAS SENSOR AND CORRESPONDING GAS SENSOR

FIELD

The present invention relates to a manufacturing method for a gas sensor, and to a corresponding gas sensor.

BACKGROUND INFORMATION

Gas sensors play an important role in safety technology, for example for the detection of carbon monoxide gas, hydrocarbons, or nitrogen oxides, for measuring motor vehicle emissions, or for monitoring the air quality of buildings.

European Patent No. EP 1192452 B1 describes a chemical sensor that is made up of a substrate on which is applied a heating element on which an electrical insulation layer is in turn applied. Located on the insulation layer is a sensor element made of metal oxide, to which an electrical signal can be transmitted via conductor paths, as well as a metal oxide layer.

Gas sensors of this kind manufactured from droplet-capable or dispensable materials, or from materials for thick-layer processes, have the advantage of high reproducibility as compared with the materials of sensors manufactured using many thin-layer processes or from nanoparticle inks. In order to obtain several contactable metal oxide layers using droplet or thick-layer processes, however, they must be applied next to one another, with the result that miniaturization of the gas sensors is not possible or is restricted.

SUMMARY

In accordance with the present invention, an example gas sensor is provided, having: a substrate; a heatable membrane configured on a substrate front side of the substrate; at least three electrodes disposed on a membrane surface of the membrane; a first coating configured on an area of the membrane surface, at least two of the at least three electrodes contacting the first coating; a second coating configured at least in part on the first coating and on an area of the membrane surface, at least two of the at least three electrodes contacting the second coating, and at least one of the at least two electrodes that contact the second coating being different from the at least two electrodes that contact the first coating.

According to a further aspect of the present invention, a manufacturing method for a gas sensor is provided, having the steps of: furnishing a substrate; configuring a heatable membrane on a substrate front side of the substrate; configuring at least three electrodes on a membrane surface of the membrane; configuring a first coating on the membrane surface, at least two of the at least three electrodes contacting the first coating; configuring a second coating at least in part on the first coating and on an area of the membrane surface, at least two of the at least three electrodes contacting the second coating and at least one of the at least two electrodes that contact the second coating being different from the at least two electrodes that contact the first coating; and configuring an opening on a substrate back side, with the result that a portion of the membrane on which the first coating and the second coating are configured is exposed.

The present invention furnishes a gas sensor that has two coatings located one above another. Both the first coating and the second coating are contacted by electrodes, so that the two coatings can each function individually as sensor layers.

An advantage of the present invention is therefore to furnish a manufacturing method for a gas sensor having several layers, the layers being individually addressable with the result that the size of the sensor can be minimized. In principle, the assemblage can be used for material from all deposition processes, optionally also for a combination of thin- and thick-layer processes.

Because the second coating is located above the first coating, the space requirement is less than with sensor layers disposed next to one another. It is therefore possible to employ inexpensive thick-layer and multi-layer methods, for example droplet and dispensing methods, in order to manufacture the gas sensor. At the same time, the present invention has the advantage of a capability for miniaturization, so that several electrically active layers can be disposed on a small space.

According to a further embodiment of the gas sensor according to the present invention, at least one of the first coating and the second coating is a metal oxide coating.

According to a further embodiment of the gas sensor according to the present invention, at least one further coating is configured on the second coating and on an area of the membrane surface, each of the at least one further coating being contacted by at least two of the at least three electrodes, at least one of those at least two electrodes respectively contacting no further coating. This has the advantage that several coatings can be disposed one above another, with the result that the space requirement of the gas sensor can be minimized and all the coatings are nevertheless individually electrically measurable.

According to a further embodiment of the gas sensor according to the present invention, the second coating is usable as a filter or as a catalyst. The filter or catalyst serves for the first coating located therebeneath. One or more cover layers can additionally be applied; this can also occur by impregnation.

According to a further embodiment of the gas sensor according to the present invention, the first coating and the second coating are of circular configuration, the second coating completely covering the first coating.

According to a further embodiment of the gas sensor according to the present invention, a first electrode end of a first electrode of the at least three electrodes is of circular-disk-shaped configuration, and the electrode ends of the electrodes, different from the first electrode, of the at least three electrodes are disposed in a circular-segment shape around the first electrode end of the first electrode, the circular-segment-shaped electrode ends of the electrodes different from the first electrode being at constant distances from the first end of the first electrode.

According to a further embodiment of the gas sensor according to the present invention, a first end of a first electrode of the at least three electrodes is of circular-disk-shaped configuration, and the ends of the electrodes, different from the first electrode, of the at least three electrodes are disposed in a circular-segment shape around the first end of the first electrode, the circular-segment-shaped ends of the electrodes different from the first electrode being at constant distances from the first end of the first electrode. This has the advantage that all the electrodes are at the most uniform possible distance from one another.

According to a further embodiment of the manufacturing method according to the present invention, at least one of the first coating and the second coating is a metal oxide coating.

According to a further embodiment of the manufacturing method according to the present invention, a region of the membrane surface is pretreated in targeted fashion prior to configuration of the first coating. For example, the region outside a region located between a first electrode of the at least three electrodes and a second electrode of the at least three electrodes can be coated with a hydrophobic material, for example a silanization. This has the advantage that upon configuration of the first coating, the first coating becomes distributed only onto the area that was not coated with the hydrophobic material. More-targeted application of the first coating is possible as a result. In particular, any desired shapes of the first coating are also possible. Conversely, regions can also be pretreated to have a coating affinity.

According to a further embodiment of the manufacturing method according to the present invention, prior to configuration of the first coating, a region of the membrane surface between a first electrode of the at least three electrodes and a second electrode of the at least three electrodes is equipped with a surface structure. This has the advantage that upon configuration of the first coating it becomes distributed only onto that region of the membrane surface which was equipped with a surface structure. In addition, the adhesive property of the first coating can be improved.

Figure 1A:
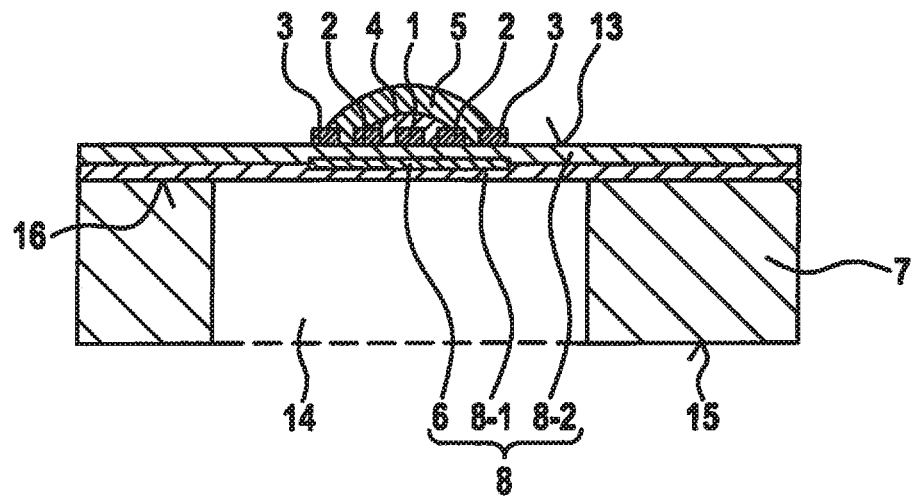
FIG. 1a is a schematic cross-sectional view to explain the structure of a gas sensor in accordance with a first embodiment of the present invention.

In all the Figures, identical or functionally identical elements and apparatuses are labeled with the same reference characters unless otherwise indicated. The numbering of method steps serves the purpose of clarity, and in particular is not intended to imply a specific sequence in time unless otherwise indicated. In particular, several method steps can also be carried out simultaneously.

DETAILED DESCRIPTION OF EXAMPLE EMBODIMENTS

FIG. 1a is a schematic cross-sectional view to explain the structure of a gas sensor in accordance with a first embodiment of the present invention. The gas sensor in accordance with the first embodiment of the present invention has a substrate 7, for example a semiconductor substrate, preferably a silicon substrate. A first membrane layer 8-1 made of an electrically nonconductive dielectric is present on a substrate front side 16 of substrate 7. A heating structure 6 that is made of an electrically conductive material is configured on first membrane layer 8-1. A second membrane layer 8-2 made of an electrically nonconductive dielectric is configured on heating structure 6 and on first membrane layer 8-1. First membrane layer 8-1, second membrane layer 8-2, and heating structure 6 form a membrane 8 having a membrane surface 13. Substrate 7 has an opening 14 on substrate back side 15, with the result that a portion of membrane 8 is exposed from the back side of a material of the substrate. Heating structure 6 is connected to a current source (not depicted) and is configured to heat a portion of membrane 8 to temperatures of, for example, 300° C.

Figure 1B:
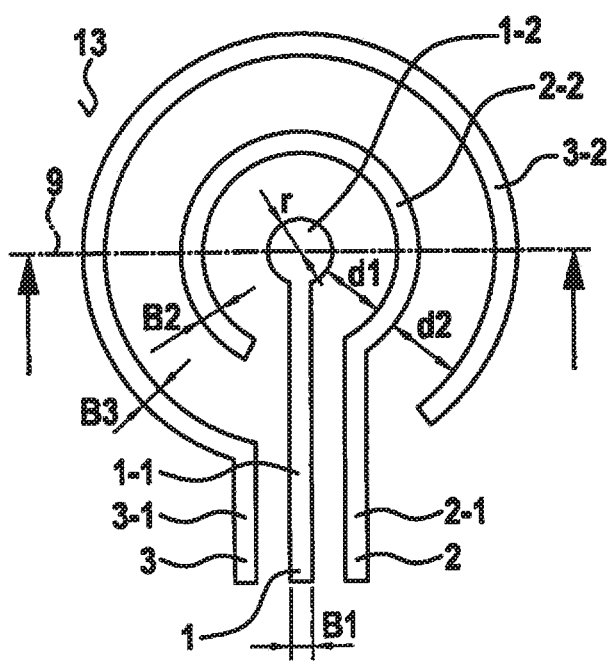
FIG. 1b is a schematic plan view of electrodes of a gas sensor in accordance with the first embodiments of the present invention.

A first electrode 1, a second electrode 2, and a third electrode 3 are configured on a portion of membrane surface 13 at which membrane 8 is exposed. The disposition of the electrodes is explained in further detail below with reference to FIG. 1b. FIG. 1b is a schematic plan view of membrane surface 13; FIG. 1a corresponds to a cross-sectional view along axis 9 shown in FIG. 1b. First electrode 1 has a linear first electrode segment 1-1 having a first electrode width B1, and a circular-disk-shaped first electrode end 1-2 having a radius r. Second electrode 2, having a second electrode width B2, has a linear second electrode segment 2-1 parallel to first electrode segment 1-1, adjoining which is a circular-segment-shaped second electrode end 2-2 disposed around first electrode end 1-2. Second electrode end 2-2 is at a constant first distance d1 from first electrode end 1-2. A third electrode 3 having a third electrode width B3 has a linear third electrode segment 3-1 parallel to first electrode segment 1-1, adjoining which is a circular-segment-shaped third electrode end 3-2 disposed around second electrode end 2-2. Third electrode end 3-2 is at a second distance d2 from second electrode end 2-2.

First distance d1 can be identical in size to second distance d2, and first electrode width B1 can be identical in size to second electrode width B2 and/or to third electrode width B3, but the present invention is not limited thereto. In particular, second electrode width B2 can be wider than first electrode width B1 and third electrode width B3.

The angles swept by circular-segment-shaped first electrode end 1-2, by circular-segment-shaped second electrode end 2-2, and by circular-segment-shaped third electrode end 3-2 are preferably greater than 180°, but are selected so that first electrode 1, second electrode 2, and third electrode 3 do not contact one another but instead are electrically insulated from one another by a material of membrane 8.

The value 2*(r+d1+B2+d2+B3) of the total diameter of the gas sensor is, for example, in the range from 50 to 200 micrometers, preferably in the range from 100 to 150 micrometers.

As shown in FIG. 1b, third electrode segment 3-1 is disposed, with reference to axis 9, to the left of first electrode segment 1-1, and first electrode segment 1-1 is disposed to the left of second electrode segment 2-1, the consequence being that second electrode end 2-2 is disposed, proceeding from second electrode segment 2-1, counterclockwise around first electrode end 1-2; and third electrode end 3-2 is disposed, proceeding from third electrode segment 3-1, clockwise around first electrode end 1-2. The present invention is not, however, limited thereto. In particular, third electrode segment 3-1 can also be located, with reference to axis 9, to the left of second electrode segment 2-1, and second electrode segment 2-1 can be located to the left of first electrode segment 1-1, so that both second electrode end 2-2 and third electrode end 3-2 are disposed clockwise around first electrode end 1-2.

The gas sensor in accordance with the first embodiment of the present invention shown in FIG. 1a furthermore has a first coating 4 that is configured on membrane surface 13. First coating 4 is of circular configuration, having a center point in first electrode end 1-2 and a radius greater than the value r+d1 and less than the value r+d1+B2, so that first coating 4 covers first electrode end 1-2 and touches, but does not completely cover, second electrode end 2-2. The width B2 of second electrode 2 is preferably selected to be sufficiently large for this. The thickness of first coating 4 is typically greatest at the center and decreases radially.

The gas sensor is configured such that by connecting first electrode 1 and second electrode 2 to two inputs of a measurement device (not shown), a resistance of an annularly shaped portion of first coating 4 located between an outer edge of first electrode end 1-2 and an inner edge of second electrode end 2-2 is measurable. The resistance of that portion of first coating 4 which is located above first electrode end 1-2, and which typically exhibits the greatest thickness, is not measurable in this context. The gas sensor is configured to detect gases, for example carbon monoxide gas, hydrocarbons, or nitrogen oxides, a change in resistance being measurable in the presence of gases, a portion of membrane 8 usefully being capable of being heated, with the aid of heating structure 6, to a temperature of, for example, 300° C.

First coating 4 can be made, for example, of a metal oxide paste that is usually manufactured by wet chemistry, for example from tin oxide $SnO_2$ nanoparticles with noble-metal doping and stabilizing additives made of further oxides, e.g. aluminum oxide $Al_2O_3$. The basic steps of manufacturing the metal oxide paste are a precipitation reaction for the basic material and for subsequent impregnations, and milling steps, e.g. in ball mills. The materials, present as powders, are then further processed using, for example, polar solvents and further milling steps, for example roller mills, to yield higher-viscosity and dispensable pastes. The present invention is not limited thereto, however; in particular, first coating 4 can also be based on copper oxide CuO and/or indium oxide and/or nickel oxide and/or cobalt oxide and/or zinc oxide.

The gas sensor in accordance with the first embodiment furthermore has a second coating 5, on first coating 4 and on an annularly shaped area around first coating 4, on membrane surface 13, which is disposed in a circular shape having a center point in first electrode end 1-2 and a radius greater than the value r+d1+B2+d2, so that second coating 5 touches second electrode end 2-2 and third electrode end 3-2. The thickness of second coating 5 is typically greatest at the center and decreases radially.

The gas sensor in accordance with the first embodiment is configured such that by connecting second electrode 2 and third electrode 3 to two inputs of a measurement device (not shown), a resistance of an annularly shaped portion of second coating 5 located between an outer edge of second electrode end 2-2 and an inner edge of third electrode end 3-2 is measurable.

Second coating 5 can be made, for example, of a metal oxide paste based on the materials recited above and manufactured by wet chemistry. The material of second coating 5 can be different from the material of first coating 4. In particular, second coating 5 can be configured as a filter and/or a catalyst for layer 4. Alternatively, for example, that portion of second coating 5 which is close to the surface can be equipped, by impregnation, with a filtering or catalyzing function.

Figure 2A:
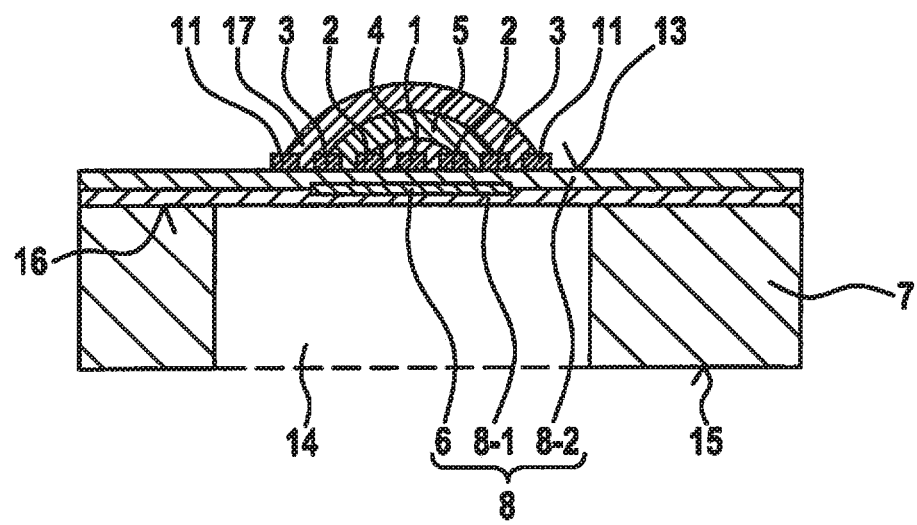
FIG. 2a is a schematic cross-sectional view to explain the structure of a gas sensor in accordance with a second embodiment of the present invention.
Figure 2B:
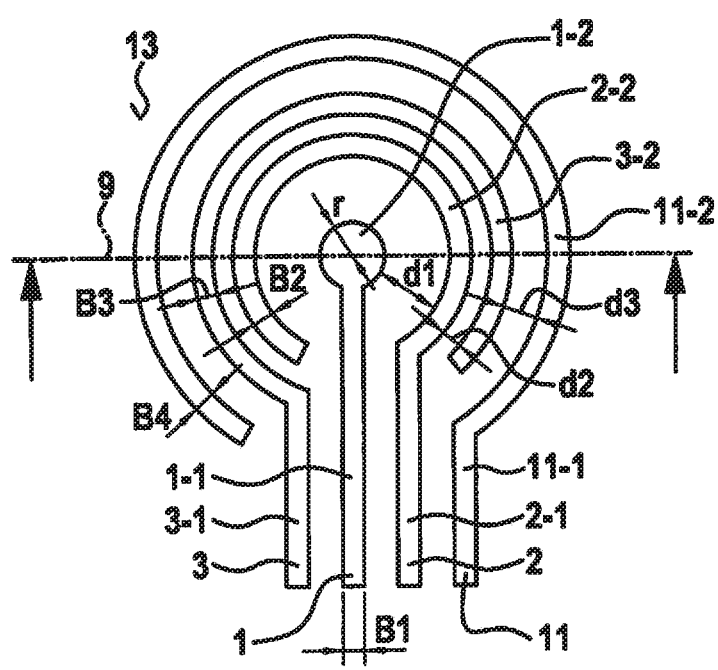
FIG. 2b is a schematic plan view of electrodes of a gas sensor in accordance with a second embodiment of the present invention.

FIG. 2a is a schematic cross-sectional view to explain the structure of a gas sensor in accordance with a second embodiment of the present invention. The second embodiment is a refinement of the first embodiment, so that the elements previously described will not be described again. In addition, a fourth electrode 11 having a fourth electrode width B4 is configured on membrane surface 13. As shown in FIG. 2b, fourth electrode 11 has a linear fourth electrode segment 11-1 that is located, with reference to axis 9, to the right of second electrode segment 2-1 and parallel to second electrode segment 2-1, adjoining which is a circular-segment-shaped fourth electrode end 11-2 disposed around third electrode end 3-2. Fourth electrode end 11-2 is at a constant third distance d3 from third electrode end 3-2. Third distance d1 can be identical in size to second distance d2 and/or to third distance d3, and fourth electrode width B4 can be identical in size to first electrode width B1, to second electrode width B2, and/or to third electrode width B3, but the present invention is not limited thereto.

In accordance with the second embodiment, second coating 5 is disposed circularly, having a center point in first electrode end 1-2 and a radius greater than the value r1+d1+B2+d2 and less than r+d1+B2+d2+B3, so that second coating 5 touches, but does not completely cover, second electrode end 2-2 and third electrode end 3-2. The gas sensor in accordance with the second embodiment furthermore has, as shown in FIG. 2a, a third coating 17 on second coating 5, and an annularly shaped area around second coating 5 on membrane surface 13 which is disposed circularly, having a center point in first electrode end 1-2 and a radius greater than the value r+d1+B2+d2+B3+d3, so that third coating 17 touches third electrode end 3-2 and fourth electrode end 11-2.

The gas sensor in accordance with the second embodiment is configured so that by connecting third electrode 3 and fourth electrode 11 to two inputs of a measurement device (not shown), a resistance of an annular portion of third coating 17 present between an outer edge of third electrode end 3-2 and an inner edge of fourth electrode end 11-2 is measurable.

Third coating 17 can be made up, for example, of a metal oxide paste based on tin oxide $SnO_2$, copper oxide CuO, and/or aluminum oxide $Al_2O_3$ and manufactured by wet chemistry. The material of third coating 17 can be different from the material of first coating 4 and from the material of second coating 5. In particular, third coating 17 can be configured as a filter and/or a catalyst.

The present invention is not limited to two or three coatings; in particular, more than three coatings can be configured on membrane surface 13, each coating being contacted by at least two electrodes.

The present invention is furthermore not limited to circular coatings, but rather the coatings can, in particular, also be square, oval, or irregular in configuration.

Figure 3:
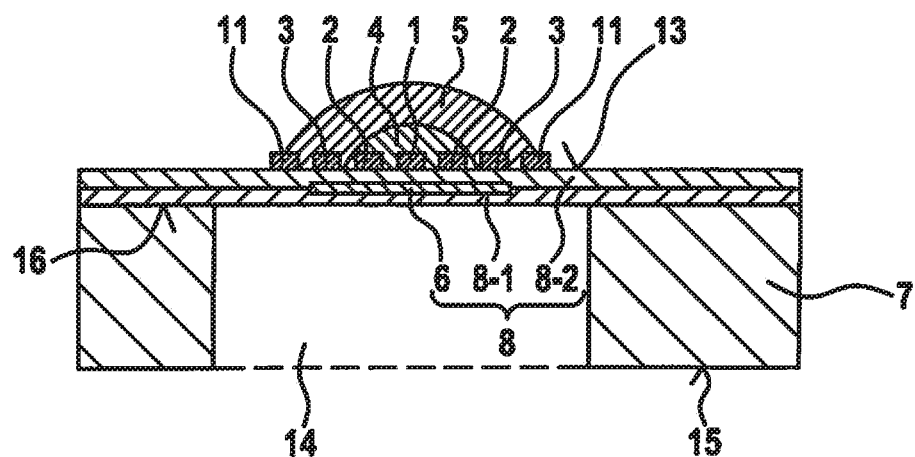
FIG. 3 is a schematic cross-sectional view to explain the structure of a gas sensor in accordance with a third embodiment of the present invention.

FIG. 3 is a schematic cross-sectional view of a gas sensor in accordance with a third embodiment of the present invention. The structure of the gas sensor corresponds to the second embodiment; in particular, the gas sensor has four electrodes as shown in FIG. 2b. In contrast to the second embodiment, third coating 17 is absent in the third embodiment. The dimensions of first coating 4 and of second coating 5 furthermore differ from the first embodiment and from the second embodiment. In accordance with the third embodiment, first coating 4 is configured circularly, having a center point in first electrode end 1-2 and a radius greater than the value r+d1+B2 and less than the value r+d1+B2+d2, so that first coating 4 completely covers first electrode end 1-2 and second electrode end 2-2. Second coating 5 is furthermore configured circularly, having a center point in first electrode end 1-2 and a radius greater than the value r+d1+B2+d2+B3+d3, so that second coating 5 covers third electrode end 3-2 and touches fourth electrode end 4-2.

The gas sensor in accordance with the third embodiment is configured such that by connecting first electrode 1 and second electrode 2 to two inputs of a measurement device (not shown), a first resistance of an annularly shaped portion of first coating 4 located between an outer edge of first electrode end 1-2 and an inner edge of second electrode end 2-2 is measurable. In addition, by connecting third electrode 3 and second electrode 11 to two inputs of a second measurement device (not shown), possibly different from the first measurement device, a second resistance of an annularly shaped portion of second coating 5 located between an outer edge of third electrode end 3-2 and an inner edge of fourth electrode end 11-2 is measurable. According to the present invention the gas sensor is configured so that the first resistance and the second resistance can be measured simultaneously.

Figure 4:
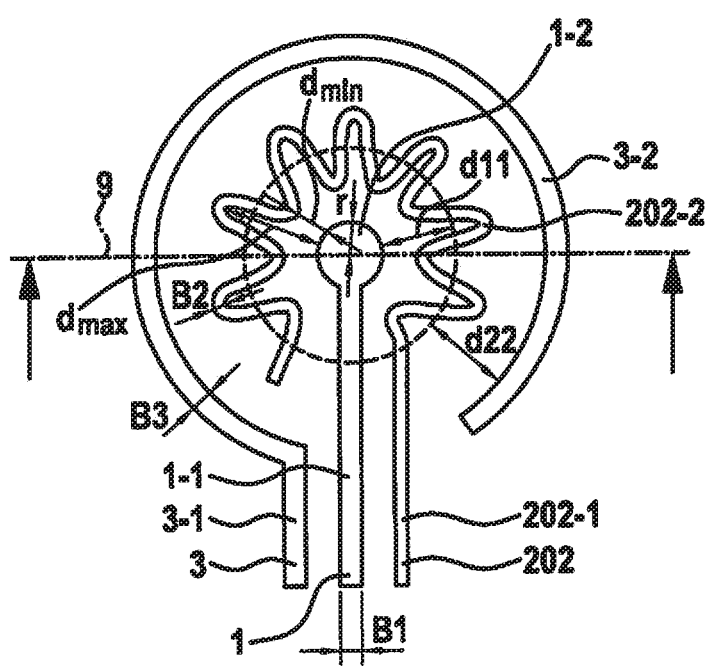
FIGS. 4, 5 are schematic plan views of electrodes of a gas sensor in accordance with further embodiments of the present invention.

FIG. 4 shows a further preferred disposition of the electrodes in accordance with a fourth embodiment of the present invention. The only difference with respect to the first embodiment of the present invention is the disposition of second electrode 202. Adjoining a linear second electrode segment 202-1 is a second electrode end 202-2 that is disposed in the shape of a wavy line along a circular segment around first electrode end 1-2. A distance of second electrode end 202-2 from first electrode end 1-2 here varies periodically between a minimum distance $d_{min}$ and a maximum distance $d_{max}$ around an average distance having the value d11−½ B2, d11 being a predefined value. Third electrode end 3-2 is at a constant distance, having the value d11+d22, from first electrode end 1-2, d22 being a predefined value. The minimum distance $d_{min}$ here is less than the maximum distance $d_{max}$, and the maximum distance $d_{max}$ is less than the value d11+d22.

Even if first coating 4 is not configured exactly circularly but instead is configured, for example, in oval or irregular fashion, in accordance with the fourth embodiment not only is first coating 4 contacted by first electrode 1 and by second electrode 2, but second coating 5 is also contacted by second electrode 2 and by third electrode 3.

The shape of second electrode segment 2-2 is not limited to the wave shape; in particular, second electrode segment 2-2 can also be disposed around first electrode end 1-2 in zigzag fashion, or with rectangular protrusions, along a circular segment.

Figure 5:
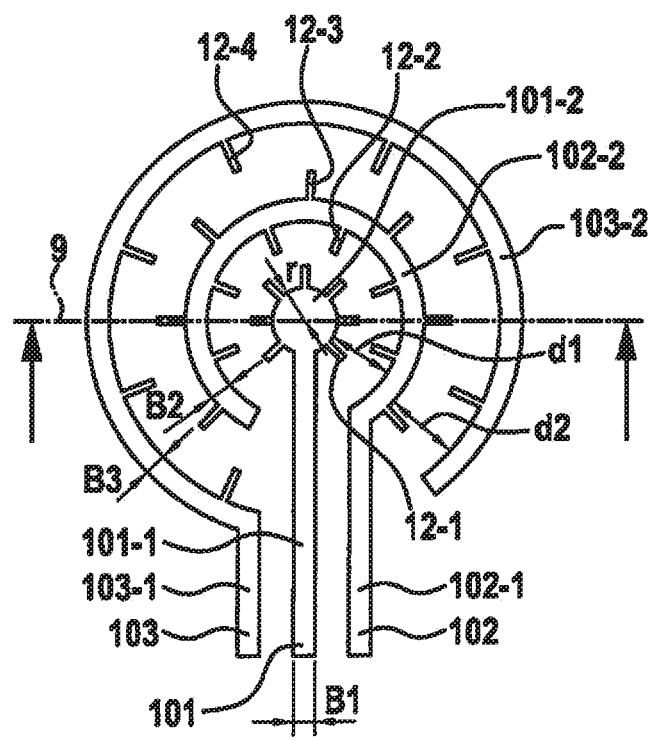

FIG. 5 shows a further preferred disposition of the electrodes in accordance with a fifth embodiment of the present invention. The fifth embodiment differs from the first embodiment only in terms of the disposition of first electrode 1, of second electrode 2, and of third electrode 3. In accordance with the fifth embodiment, a first electrode 101 has a linear first electrode segment 101-1 having a first electrode width B1 and a circular-disk-shaped first electrode end 101-2 having a radius r. Second electrode 102, having a second electrode width B2, has a linear second electrode segment 102-1 parallel to first electrode segment 101-1, adjoining which is a circular-segment-shaped second electrode end 102-2 disposed around first electrode end 101-2. Second electrode end 102-2 is at a constant first distance d1 from first electrode end 101-2. A third electrode 3, having a third electrode width B3, has a linear third electrode segment 103-1 parallel to first electrode segment 101-1, adjoining which is a third electrode end 103-2 disposed around second electrode end 102-2. Third electrode end 103-2 is at a second distance d2 from second electrode end 102-2. In addition, first electrode 101 has a plurality of first bars 12-1 that are disposed on first electrode end 101-2 in a radial direction of circular-disk-shaped first electrode end 101-2. Second electrode 102 has a plurality of second bars 12-2 that are disposed toward first electrode end 101-2, in a direction perpendicular to second electrode end 102-2, on second electrode end 102-2. Second electrode 102 has a plurality of third bars 12-3 that are disposed toward third electrode end 103-2, in a direction perpendicular to second electrode end 102-2, on second electrode end 102-2. The third electrode has a plurality of fourth bars 12-4 that are disposed toward second electrode end 102-2, in a direction perpendicular to third electrode end 103-2, on third electrode end 103-2. First bars 12-1 and second bars 12-2 have an extent less than a value ½ d1, and third bars 12-3 and fourth bars 12-4 have an extent less than a value ½ d2. First to fourth bars 12-1 to 12-4 can have a rectangular, triangular, or irregular outline. The present invention is not limited to the present form; in particular, first bars 12-1 and fourth bars 12-4 can be absent.

Even if first coating 4 is not configured exactly circularly but instead is disposed, for example, in oval or irregular fashion, in accordance with the fifth embodiment not only is first coating 4 contacted by first electrode 1 and by second electrode 2, but second coating 5 is also contacted by second electrode 2 and by third electrode 3.

Figure 6:
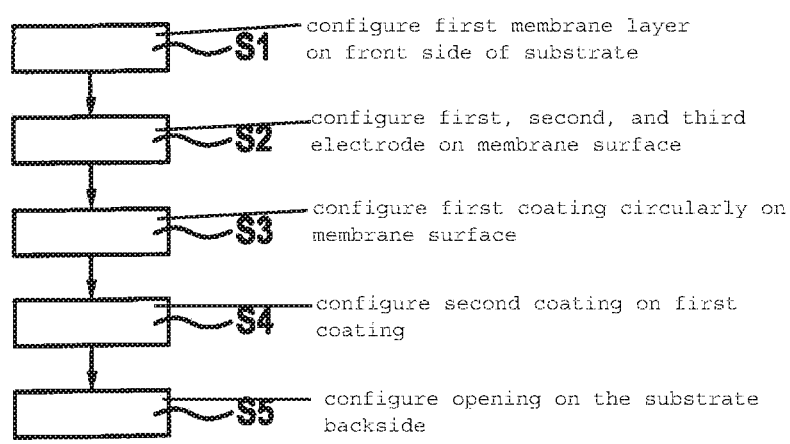
FIG. 6 is a flow chart to explain a manufacturing method for a gas sensor.

FIG. 6 is a flow chart to explain a manufacturing method for a gas sensor.

In a first step S1, a first membrane layer 8-1 made of an electrically nonconductive dielectric is configured on a substrate front side 16 of a substrate 7, for example of a semiconductor substrate, preferably of a silicon substrate. A heating structure 6 that is made of an electrically conductive material is configured on first membrane layer 8-1. A second membrane layer 8-2 made of an electrically nonconductive dielectric is configured on heating structure 6 and on first membrane layer 8-1. First membrane layer 8-1, second membrane layer 8-2, and heating structure 6 form a membrane 8 having a membrane surface 13.

In a second step S2, a first electrode 1 having a first electrode segment 1-1 and a first electrode end 1-2, a second electrode 2 having a second electrode segment 2-1 and a second electrode end 2-2, and a third electrode 3 having a third electrode segment 3-1 and a third electrode end 3-2 are configured on membrane surface 13. The disposition of the electrodes here corresponds to the disposition shown in FIG. 1*b* and therefore will not be repeated here.

In a third step S3, a first coating 4 is configured circularly on membrane surface 13, having a center point in first electrode end 1-2 and having a radius greater than the value r+d1 and less than r+d1+B2, so that first coating 4 covers first electrode end 1-2 and touches but does not completely cover second electrode end 2-2. First coating 4 can be constituted, for example, using a droplet method or a dispensing method.

First coating 4 can be manufactured, for example, from a metal oxide paste manufactured by wet chemistry, which is usually by wet chemistry, for example, from tin oxide $SnO_2$ nanoparticles having noble-metal doping and stabilizing additives made of further oxides, e.g., aluminum oxide $Al_2O_3$. The present invention is not limited thereto, however; in particular, first coating 4 can also be based on copper oxide CuO and/or indium oxide and/or nickel oxide and/or cobalt oxide and/or zinc oxide.

A first drying step and/or a burning-out step can already be accomplished after the application of first coating 4. After the burning-out step, first coating 4 is solid and gas-sensitive and exhibits high porosity.

In a fourth step S4, a second coating 5 is configured on first coating 4, and an annularly shaped area around first coating 4 is configured circularly on membrane surface 13, having a center point in first electrode end 1-2 and a radius greater than the value r+d1+B2+d2, so that second coating 5 touches second electrode end 2-2 and third electrode end 3-2. Second coating 5 can be configured, for example, using a droplet method or a dispensing method.

After the application of second coating 5, either a further or a shared drying step and/or a burning-out step can be accomplished for coating 4 and 5. After the burning-out step, both coatings 4 and 5 are then solid and gas-sensitive and exhibit high porosity.

In a fifth step S5, an opening 14 is configured on a substrate back side 15 of substrate 7, with the result that a portion of membrane 8 on which first coating 4 and second coating 5 are configured is exposed. Opening 14 can be formed, for example, by an etching process, by milling, or with the aid of a laser.

In accordance with a further preferred embodiment, prior to application of the first coating an additional coating with a hydrophobic material, for example a silanization, is configured in a region located outside second electrode end 2-2. The material of first coating 4 preferably encompasses a solvent, for example a polar polyalcohol. Upon configuration of first coating 4, first coating 4 will preferably become deposited not on the additional coating but instead in a region located within second electrode end 2-2. The additional coating, as well as the solvent contained in the material of first coating 4, will volatilize in a further heating step using heating apparatus 6.

In accordance with a further preferred embodiment, prior to application of the first coating a surface structuring is configured, for example using an etching process or deposition process, in a region located between first electrode end 1-2 and second electrode end 2-2. Upon configuration of first coating 4, first coating 4 will preferably become deposited on the surface structuring. The surface structuring can also refer to first electrode end 1-2 and second electrode end 2-2 themselves.

In accordance with a further preferred embodiment, after the application of first coating 4 and prior to the application of second coating 5 a further additional coating is configured in a region located outside third electrode end 3-2.

In accordance with a further preferred embodiment, after the application of first coating 4 and prior to the application of second coating 5 a further surface structuring is configured in a region located between second electrode end 2-2 and third electrode end 3-2.

The present invention is not limited to the specific forms; in particular, the disposition of first electrode 1, of second electrode 2, and of third electrode 3 can correspond to one of the dispositions shown in FIG. 2b, FIG. 4, or FIG. 5.

Further coatings can furthermore also be configured, each further coating preferably being contacted by at least two electrodes.

Although the present invention has been described above with reference to preferred exemplifying embodiments it is not limited thereto, but instead is modifiable in a multiplicity of ways. In particular, the present invention can be changed or modified in numerous ways without deviating from the essence of the present invention.

What is claimed is:

1. A gas sensor, comprising:
    a substrate;
    a heatable membrane configured on a substrate front side of the substrate;
    at least three electrodes disposed on a membrane surface of the membrane;
    a first coating configured on an area of the membrane surface, at least two of the at least three electrodes being in direct contact with the first coating;
    a second coating configured at least in part on the first coating and on an area of the membrane surface, at least two of the at least three electrodes being in direct contact with the second coating, and at least one of the at least two electrodes that are in direct contact with the second coating being different from the at least two electrodes that are in direct contact with the first coating;
    wherein the first coating and the second coating are of circular configuration, the second coating completely covering the first coating;
    wherein at least one of the at least two electrodes that are in direct contact with the first coating is not in direct contact with the second coating.

2. The gas sensor as recited in claim 1, wherein at least one of the first coating and the second coating is a metal oxide coating.

3. The gas sensor as recited in claim 1, further comprising:
    at least one further coating configured on the second coating and on an area of the membrane surface, each of the at least one further coating being in direct contact with at least two of the at least three electrodes, at least one of the at least two electrodes that are in direct contact with the at least one further coating respectively contacting no further coating;
    wherein the at least one of the at least two electrodes that are in direct contact with the at least one further coating: (i) is not in direct contact with the second coating, and (ii) is not in direct contact with the first coating.

4. The gas sensor as recited in claim 1, wherein the second coating is usable as a filter or as a catalyst.

5. The gas sensor as recited in claim 1, wherein a first electrode end of a first electrode of the at least three electrodes being of circular-disk-shaped configuration, and electrode ends of the electrodes, different from the first electrode, of the at least three electrodes being disposed in a circular-segment shape around the first electrode end of the first electrode, the circular-segment-shaped electrode ends of the electrodes different from the first electrode being at constant distances from the first end of the first electrode.

6. The gas sensor as recited in claim 1, wherein at least one of the at least two electrodes that are in direct contact with the second coating is not in direct contact with the first coating.

7. The gas sensor as recited in claim 1, wherein the first coating and the second coating are made from a metal oxide paste.

* * * * *